United States Patent
Lagerqvist (10) Patent No.: US 12,427,216 B2
(45) Date of Patent: Sep. 30, 2025

(54) METHOD OF FILLING A MEDICAL WASHER/DISINFECTOR

(71) Applicant: Getinge Disinfection AB, Vaxjo (SE)

(72) Inventor: Carl-Johan Lagerqvist, Vaxjo (SE)

(73) Assignee: GETINGE DISINFECTION AB, Vaxjo (SE)

( * ) Notice: Subject to any disclaimer, the term of this patent is extended or adjusted under 35 U.S.C. 154(b) by 282 days.

(21) Appl. No.: 17/933,285

(22) Filed: Sep. 19, 2022

(65) Prior Publication Data
US 2023/0087279 A1   Mar. 23, 2023

(30) Foreign Application Priority Data
Sep. 21, 2021   (EP) .................................. 21197895

(51) Int. Cl.
| | |
|---|---|
| *A61L 2/00* | (2006.01) |
| *A61B 90/70* | (2016.01) |
| *A61L 2/18* | (2006.01) |
| *A61L 2/24* | (2006.01) |
| *B08B 3/02* | (2006.01) |

(Continued)

(52) U.S. Cl.
CPC ................ *A61L 2/24* (2013.01); *A61B 90/70* (2016.02); *A61L 2/0082* (2013.01); *A61L 2/0088* (2013.01); *A61L 2/18* (2013.01); *B08B 3/02* (2013.01); *B08B 3/08* (2013.01); *F04D 15/0066* (2013.01); *F04D 15/0209* (2013.01); *A61L 2202/122* (2013.01); *A61L 2202/14* (2013.01); *A61L 2202/15* (2013.01); *A61L 2202/17* (2013.01); *A61L 2202/24* (2013.01); *B08B 2203/027* (2013.01); *F04D 15/00* (2013.01); *F04D 15/0027* (2013.01);
(Continued)

(58) Field of Classification Search
CPC ......... A61B 1/121; A61B 1/123; A61B 1/125; A61L 2202/17; A61L 2202/24
See application file for complete search history.

(56) References Cited

U.S. PATENT DOCUMENTS

2011/0297189 A1* 12/2011 Gram .................. A47L 15/0023
                                                           134/25.2
2016/0242636 A1*  8/2016 Kawachi .................. B08B 3/04
(Continued)

FOREIGN PATENT DOCUMENTS

CN   107900011 A  *  4/2018
EP   0943282 A2   *  9/1999

*Primary Examiner* — Kaj K Olsen
*Assistant Examiner* — Richard Z. Zhang
(74) *Attorney, Agent, or Firm* — McCoy Russell LLP (57) ABSTRACT

The invention relates to method of filling a medical washer/disinfector. A desired pump speed of a circulation pump is determined. A predefined filling level associated with the desired pump speed is identified. Liquid is fed into a washing chamber while the circulation pump is running at less than said desired pump speed. While the liquid is continued to be fed so that the liquid level rises, the pump speed is increased based on the rising liquid level until said desired pump speed is reached. When the pump is running at said desired pump speed, it is detected when the liquid has been filled to the predefined filling level, and upon such detection the feeding of the liquid into the washing chamber is interrupted. Then invention also relates to a method of operating a medical washer/disinfector, a control unit and a medical washer/disinfector.

13 Claims, 4 Drawing Sheets

(51) Int. Cl.
  *B08B 3/08* (2006.01)
  *F04D 15/00* (2006.01)
  *F04D 15/02* (2006.01)
  *G01F 23/00* (2022.01)
  *G05D 7/00* (2006.01)
  *G05D 9/00* (2006.01)
(52) U.S. Cl.
  CPC ............... *G01F 23/00* (2013.01); *G05D 7/00* (2013.01); *G05D 9/00* (2013.01)

(56) References Cited

U.S. PATENT DOCUMENTS

2019/0203396 A1\* 7/2019 Im ........................... D06F 23/06
2020/0255998 A1\* 8/2020 Woodhead .......... A47L 15/0047

\* cited by examiner

METHOD OF FILLING A MEDICAL WASHER/DISINFECTOR

Benefit and priority are claimed to EP21197895.2, filed Sep. 21, 2021.

TECHNICAL FIELD

The present disclosure relates to a method of filling a medical washer/disinfector. The present disclosure also relates to a method of operating a medical washer/disinfector for which said method of filling is used. The present disclosure further relates to a control unit for controlling performance of said methods and to a medical washer/disinfector which comprises such a control unit. Washer/disinfectors can be used for processing used medical goods in a hospital central sterile services department (CSSD), for example.

BACKGROUND ART

Medical washers/disinfectors may typically be provided at dental clinics, surgical departments, central sterile supply departments, and similar facilities. The medical washers/disinfectors may be used for washing/disinfecting a wide range of different medical articles, such as recirculated goods, tubular instruments, surgical sets, anaesthetic items, laboratory items, bedpans, etc. In other words, a washer/disinfector should be able to handle a large variety of different type of goods, which means that sometimes a smaller load size will be processed, and at other occasions a larger load size will be processed. Medical washer/disinfectors are commonly intended to provide both cleaning of visible physical contaminants from medical devices or medical equipment, as well as a degree of disinfection, such as by hot water exposure and/or cleaning/disinfection agents. Washing/disinfection processes for each batch of goods commonly include more than one phase. For example, they can include some or all of pre-rinse cycles, one or more washing cycles with various detergents and cleaning agents, one or more rinses, and/or a hot "thermal rinse" for disinfection. In some applications, the washing chamber will be drained at the end of each phase, and new liquid is added for the subsequent phase. Different phases can use different types of liquids, and different liquid circulation patterns.

In order to be able to handle different load scenarios (e.g. goods that are lightly soiled or heavily soiled, different dimensions of goods, or different numbers of goods), conventional medical washers/disinfectors are dimensioned with respect to the largest load that they are designed for. This means that when smaller loads are processed, the conventional medical washers/disinfectors use higher water pressure and larger water flow than what is really necessary for a satisfactory result. Thus, the water consumption, and consequently also the amount of detergent and heating energy used, will be higher than required. Such excess consumption is neither desirable from an environmental perspective, nor from energy and economical perspectives.

SUMMARY OF THE INVENTION

An object of the present disclosure is to mitigate the above mentioned drawbacks of conventional washers/disinfectors. This and other objects, which will become apparent in the following, are accomplished by a method as defined in claim 1. Exemplary embodiments are presented in the dependent claims.

The general inventive concept is based on the realization that different loads may require different degrees of cleaning effort. For example, small or lightly soiled loads may be cleaned with less pressure and less flow. The inventor has realized that by adapting the cleaning effort to the load, e.g. the load size and/or the soiling level, excess consumption of water, energy, and detergent, can be avoided, thus providing a more environmentally friendly, energy-saving and economical solution. In particular, the inventor has realized that pump speed affects the water level needed for effective pumping and circulation in the washing chamber of the medical washer/disinfector. Assuming all other factors being the same, a higher pump speed will "pull" more water, thus creating a lower water level in the washing chamber, than a lower pump speed. Therefore, the inventor has suggested that a higher desired pump speed should be associated with a higher predefined filling level, while a lower desired pump speed should be associated with a lower predefined filling level. For example, a user who has loaded the medical washer/disinfector may select a program based on the load size and/or the soiling level, and that program may thus be associated with a desired pump speed, which in turn is associated with a predefined filling level.

Furthermore, the inventor has realized that different types of goods will hold or bind different amounts of water when water is supplied to the washing chamber. For example larger loads, or a load having goods with many cavities (e.g. catheters and other tubular instruments), may keep more of the circulating water than other goods. This means that even though the same amount of water would be supplied to the washer/disinfector each time, and even though the same pump speed would be used each time, the water level in the washing chamber will depend on what goods are present in the washing chamber and how much water they collectively hold.

By increasing the pump speed in a controlled manner based on the rising liquid level (rather than immediately starting with the desired pump speed), you can avoid cavitation effects and pressure strokes, which could otherwise occur because if much water gets stuck on the goods and does not fall down to the bottom of the washing chamber.

The above ideas related to the general inventive concept will be further discussed below with respect to different aspects and exemplary embodiments.

According to a first aspect of the present inventive concept, there is provided a method of filling a medical washer/disinfector having a washing chamber for receiving medical articles to be washed/disinfected and a circulation pump for circulating a liquid to and from the washing chamber, the method comprising:

- determining a desired pump speed for a phase of a process cycle,
- identifying a predefined filling level in the washing chamber associated with the desired pump speed,
- feeding liquid into the washing chamber while the circulation pump is running at less than said desired pump speed,
- while continuing to feed liquid into the washing chamber so that the liquid level rises, controlling the pump speed to be increased based on the rising liquid level until said desired pump speed is reached,
- when the pump is running at said desired pump speed, detecting when the liquid has been filled to the predefined filling level in the washing chamber, and
- upon detection that the liquid has been filled to the predefined filling level, interrupting the feeding of the liquid into the washing chamber.

By providing a filling method in which the pump speed is increased, in a controlled manner based on the rising liquid level, to a desired pump speed, and by associated a predefined filling level with said desired pump speed, an efficient filling method is achieved which saves water and detergent compared to prior art filling methods.

It should be understood that a process cycle may include several different phases, such as washing, disinfecting, draining, rinsing, drying, etc. Different phases may call for different desired pump speeds. Thus, depending on the particular phase a certain desired pump speed may be determined which is different from the desired pump speed of a later phase of the process cycle when liquid is once more fed into the washing chamber. Accordingly, the predefined filling level associated with a desired pump speed for one phase may be different from the predefined filling level associated with another desired pump speed for another phase. Furthermore, it should be understood that different process cycles may have different numbers and types of phases.

The liquid used in the method of filling may typically be water, such as cold water, hot water and/or deionized water.

It should be understood that the step of feeding liquid into the washing chamber while the circulation pump is running may be preceded by previous feeding of liquid into the washing chamber. For example, if the washing chamber is completely empty of liquid, then liquid is suitably supplied to a certain level before the circulation pump is started. When the circulation pump is started it is run at a speed which is less than the desired pump speed, and the liquid is simultaneously fed into the washing chamber. As the liquid level rises the pump speed may be increased. The increase in pump speed may be performed continuously or in discrete steps, or a combination thereof.

From the above, it can be understood that, according to at least one exemplary embodiment, the step of feeding liquid into the washing chamber is preceded by the steps of:
  initially supplying liquid to the washing chamber while the circulation pump is inactive,
  detecting that the liquid has reached a predefined pump-starting level in the washing chamber, and
  activating the circulation pump at less than said desired pump speed when the liquid has reached the predefined pump-starting level.

By postponing the activation of the circulation pump until a predefined pump-starting level is reached, it can be ensured that for a certain starting speed of the circulation pump there will be enough liquid for the pumping of liquid to go smoothly with low risk of cavitation effects. In particular, when the circulation pump is started, liquid will be pulled by the pump from the bottom of the washing chamber and displaced into pipes for distribution to, for example, spray wings, nozzles or similar components in the washing chamber. The pulling of the liquid may thus cause the liquid level to be lowered somewhat, before it rises again as the fluid is continued to fed. By appropriately balancing the pump speed with the liquid level, the risk of the liquid level falling too much avoids the risk of cavitation. As more liquid is feed into the washing chamber, the pump speed may be increased.

According to at least one exemplary embodiment, the step of controlling the pump speed to be increased based on the rising liquid level comprises:
  filling the washing chamber to a series of specific levels and increasing the pump speed for each specific level that is reached.

By having checkpoints in the form of specific levels, a simple and efficient control of the pump speed is achievable. Each specific level may suitably be associated with a designated corresponding pump speed. In some exemplary embodiments it is conceivable that there is no speed increase between the specific levels, but only when a next specific level is reached. In other exemplary embodiments the pump speed may be increased at a relatively slow rate also between two consecutive specific levels. The rate should be slow enough so that the designated pump speed for the next level is not reached prematurely. In some exemplary embodiments the rate at which the pump speed is increased may be controlled based on a measured flow of liquid being fed into the washing chamber. For example, the rate at which the pump speed increases may be proportional to the flow rate at which the liquid is fed into the washing chamber.

From the above it can be understood that, according to at least one exemplary embodiment, the step of controlling the pump speed to be increased based on the rising liquid level comprises:
  continuously increasing the pump speed between any two specific levels of said series of specific levels.

As previously explained, this provides a simple and efficient controlling of the filling process.

In at least some exemplary embodiments, there may suitably be a safety margin relative to the predefined filling level. The reason for this is that once the feeding of the liquid has stopped and the liquid level has stabilized, then the stabilized level may actually have dropped to compared to the level at which the feeding was stopped, for example due to pumped liquid in the pumping system and staying on goods and not falling back to the liquid bulk in the washing chamber. Therefore, if the feeding is stopped precisely when the predefined filling level has been reached, then there may be a risk that in some cases the liquid level will drop below the predefined filling level (due to continued pumping), which in turn may result in too little liquid at the bottom of the washing chamber for the associated desired pump speed, which may therefore cause cavitation and loss of performance. Accordingly, in at least some exemplary embodiments there may be a time delay, so that when it is detected that the predefined filling level has been reached, the feeding is continued for a short time before the feeding is interrupted, thus creating a safety margin. The safety margin and the time delay does not necessarily need to be the same for each case. For instance, in at least some exemplary embodiments the time delay/safety margin may be based on the currently determined desired pump speed and/or the predefined filling level associated therewith. These considerations are at least partly reflected in the below presented exemplary embodiment.

Thus, according to at least one exemplary embodiment, said step of interrupting the feeding of the liquid into the washing chamber is performed a predefined time period after detecting that the liquid has reached the predefined filling level, such as after 0.5-10 seconds, suitably 1-5 seconds, for example 1.5-3 seconds, the method further comprising, after interrupting the feeding of the liquid into the washing chamber,
  allowing the liquid level in the washing chamber to stabilize while the circulation pump is running, and
  if the stabilized liquid level is below the predefined filling level, feeding more liquid into the washing chamber in order to reach the predefined filling level.

The advantage of being able to compensate for a dropping level is that the safety margin does not have to be too large, thus avoiding using liquid in excess. Should the predefined time period be too short for the particular load in the washing chamber it can thus be compensated by feeding more liquid into the washing chamber after the liquid level has stabilized. The time allowed for the liquid level to stabilize is normally longer than said predefined time period. For example, time allowed for the liquid level to stabilize may suitably be more than 10 seconds, such as 15-30 seconds.

According to at least one exemplary embodiment, the method further comprises:
- determining for said phase of a process cycle a desired chemical concentration of an additive in the washing chamber,
- measuring, by means of a flow sensor, the volume of the liquid that is fed into the washing chamber,
- based on the measured volume, determining an amount of said additive to be provided into the washing chamber for obtaining said desired chemical concentration, and
- providing said determined amount of additive into the washing chamber.

As already understood from the above discussion, by having a controlled filling of liquid, over-consumption of the liquid can be avoided. By adapting the amount of additive to the volume of liquid supplied to the washing chamber, over-consumption of the additive can also be avoided. The additive may typically be a detergent or a rinsing agent. The amount of detergent added may, for example, be controlled by using a detergent flow meter and a dosing pump.

According to at least one exemplary embodiment, said desired pump speed for the circulation pump is less than the maximum working speed for the circulation pump. This may typically be the case for lightly soiled goods or for smaller loads. As previously explained, lower pump speed is associated with lower predefined filling level, and thus overconsumption may be avoided without loss of performance. Indeed also for larger loads, the desired pump speed may be less than the maximum working speed for the circulation pump. Suitably, there may be a plurality of different available desired pump speeds selectable for different degrees of soiling and/or different load sizes. However, it should be understood that in at least some exemplary embodiments, the desired pump speed may correspond to the maximum working speed for the circulation pump, such as for heavily soiled and/or large loads.

According to at least one exemplary embodiment, the method further comprises running a washing/disinfection cycle after said filling of the medical washer/disinfector, wherein said desired pump speed is the maximum speed used for the circulation pump during the washing/disinfection cycle. This is advantageous since the actual supplying of liquid and the subsequent use of the liquid are appropriate matched with each other.

According to at least one exemplary embodiment, the circulation pump is a first circulation pump, the medical washer/disinfector also having a second circulation pump for use after the filling has been completed, the method comprising:
- keeping the second circulation pump inactive during the feeding of liquid into the washing chamber.

Providing two circulation pumps may be advantageous as they may, for example, be used for pumping liquid to different parts of the washing chamber. However, by keeping the second circulation pump inactive during the feeding of liquid into the washing chamber, it will not steal liquid from the first circulation pump, thus avoiding cavitation and loss of performance. The first circulation pump may suitably be configured and dimensioned to provide a higher maximum pressure and flow than the second circulation pump. Thus in some embodiments, the second circulation pump has a lower pumping capacity than the first circulation pump, so that the water level is optimized for the capacity and intended running speed of the larger first pump only, to minimize water usage. For example, the final liquid level is only sufficient to run the first pump at the maximum desired speed for the phase of the process cycle if the second pump is turned off, and the first pump must be slowed down or turned off to run the second pump.

After the feeding has been completed, and after any subsequent compensational supplying of liquid due to the stabilized liquid level dropping too low, the first and the second circulation pump may suitably be run alternatingly. For examples, when one is running the other one is turned completely off. In at least some exemplary embodiments in which the desired pump speed (of the first circulation pump) is at a higher flow rate than the maximum flow rate achievable by the second circulation pump (i.e. when the second circulation pump runs at full speed), then the first circulation pump may suitably run at a lower speed than the desired pump speed even though the second circulation pump is also running. Such lower speed of the first circulation pump is suitably calculated so that the resulting total flow rate corresponds to or is slightly lower than what the flow rate that would be if only the first circulation pump is run at said desired pump speed. In this manner the risk of the liquid level dropping too low during operation may be avoided, without filling unnecessarily large amounts of liquid into the washing chamber. From the above, it can be understood that by alternating the operation of the circulation pumps (or at least lowering the speed of the first circulation pump when the second circulation pump is running, liquid and additive consumption may be kept low, without compromising on quality. These considerations are at least partly reflected in the following exemplary embodiment.

According to at least one exemplary embodiment, the washer/disinfector is sized and configured to receive a wash cart holding medical articles to be washed/disinfected in the washing chamber, said wash cart including one or more wash cart sprayers;
- wherein the washer/disinfector comprises one or more chamber sprayers on the ceiling and/or walls of the washing chamber;
- wherein the washer/disinfector is configured to selectively circulate liquid to the chamber sprayers and/or to the wash cart sprayers when present using a first circulation pump and a second circulation pump, the first circulation pump and the second circulation pump being separately controllable,
- wherein the first circulation pump is a wash cart sprayer pump and the second circulation pump is a chamber sprayer pump, and wherein the liquid level obtained during the filling process is based on the liquid level requirements when only the wash cart sprayer pump is running during a subsequent washing/disinfecting process.

By dimensioning the liquid consumption based on envisaged use of the wash cart sprayer pump (first circulation pump), which suitably has greater capacity than the chamber sprayer pump (second circulation pump), the liquid consumption can be kept low. By lowering the speed of or completely shutting off the wash cart sprayer pump when the chamber sprayer pump is running, the risk of cavitation and performance loss can be avoided.

According to at least one exemplary embodiment, the first circulation pump is configured to be controllable between 0-100% of its maximum speed. Suitably, any number within that range is obtainable, e.g. by using a stepless motor. However, it is conceivable that in other exemplary embodiments, the first circulation pump is controllable between 0-100% of its maximum speed in discrete steps. The second circulation pump may, in its simplest form, just have two states, i.e. on or off. However, similarly to the first circulation pump, having a second circulation pump which is controllable within the range of 0-100% of its maximum speed may also be an option.

According to a second aspect of the present inventive concept, there is provided a method of operating a medical washer/disinfector having a washing chamber for receiving medical articles to be washed/disinfected and a circulation pump for circulating a liquid to and from the washing chamber, the method comprising:

filling the washing chamber by performing the method according to the first aspect, including any embodiment thereof, wherein the circulation pump is a first circulation pump, the medical washer/disinfector further having a second circulation pump, wherein the method of operating the medical washer/disinfector further comprises:

keeping the second circulation pump inactive during the feeding of liquid into the washing chamber, and after the filling of liquid in the washing chamber has been completed, alternating between activation and inactivation of the second circulation pump in such manner that when the second circulation pump is running, the first circulation pump is controlled to run at a speed that is lower than said desired pump speed or to be inactivated.

The advantages of the operating method of the second aspect largely correspond to the advantages of the filling method of the first aspect, including any embodiments thereof.

According to a third aspect of the present inventive concept, there is provided a control unit for controlling performance of the steps of the filling method of the first aspect and/or the operating method of the second aspect, including any embodiments thereof.

The advantages of the control unit of the third aspect largely correspond to the advantages of the filling method of the first aspect and/or the operating method of the second aspect, including any embodiments thereof.

The control unit may include a microprocessor, microcontroller, programmable digital signal processor or another programmable device. The control unit may also, or instead, include an application specific integrated circuit, a programmable gate array or programmable array logic, a programmable logic device, or a digital signal processor. Where it includes a programmable device such as the microprocessor, microcontroller or programmable digital signal processor mentioned above, the processor may further include computer executable code that controls operation of the programmable device. The control unit is preferably configured for use with medical washer/disinfectors, and provided with electronic instructions to perform and control any of the methods described herein.

According to a fourth aspect of the present inventive concept, there is provided a medical washer/disinfector, comprising a washing chamber for receiving medical articles to be washed/disinfected, one or more circulation pumps for circulating a liquid to and from the washing chamber, and a control unit according to the third aspect, including any embodiment thereof.

The medical washer/disinfector may also include at least one door for accessing the washing chamber.

The advantages of the medical washer/disinfector of the fourth aspect largely correspond to the advantages of the control unit of the third aspect, including any embodiment thereof.

According to at least one exemplary embodiment of the medical washer/disinfector, the washer/disinfector is sized and configured to receive a wash cart holding medical articles to be washed/disinfected in the washing chamber, said wash cart including one or more wash cart sprayers;

wherein the washer/disinfector comprises one or more chamber sprayers on the ceiling and/or walls of the washing chamber;

wherein the washer/disinfector is configured to selectively circulate liquid to the chamber sprayers and/or to the wash cart sprayers when present using a first circulation pump and a second circulation pump, the first circulation pump and the second circulation pump being separately controllable. Wash carts typically have wheels and can be rolled into and out of washing chambers while holding a load of medical articles. Some wash carts are connectable to a pumped liquid source when in a washing chamber, for spraying liquid on the medical articles it holds.

It should be understood that although the above first, second, third and fourth aspects have been described in connection with a medical washer/disinfector, the corresponding inventive principles would be implementable also for other types of apparatus, such as household washers.

Therefore, it can be understood that, in a general sense, according to a fifth aspect of the present inventive concept there is provided a method of filling a washer having a washing chamber for receiving articles to be washed and a circulation pump for circulating a liquid to and from the washing chamber, the method comprising the corresponding steps as presented for the filling method of the first aspect. Similarly, other steps in the embodiments of the filling method of the first aspect may be freely implemented in the method of filling a washer according to the fifth aspect.

In addition to the above, it should be understood that, in a general sense, according to a sixth aspect there is provided a method of operating a washer which, except for not relating to a medical washer/disinfector specifically, includes the same features and embodiments as the method of the second aspect; according to a seventh aspect there is provided a control unit which, except for not relating to a medical washer/disinfector specifically, includes the same features and embodiments as the control unit of the third aspect; and according to an eighth aspect there is provided a washer which, except for not relating to a medical washer/disinfector specifically, includes the same features and embodiments as the medical washer/disinfector of the fourth aspect.

Any of the washer/disinfectors discussed herein may include a door for accessing the washing chamber. They may optionally be pass-through washer/disinfectors including a loading door and an unloading door, in particular for loading and unloading dirty and clean medical goods (respectively) on opposite sides of a dividing wall.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated. Further features of, and advantages with, the present invention will become apparent when studying the appended claims and the following description. The skilled person realizes that different features of the present invention may be combined to create embodiments other than those described in the following, without departing from the scope of the present inventive concept.

DETAILED DESCRIPTION

The present inventive concept will now be described more fully hereinafter with reference to the accompanying drawings, in which certain aspects of the inventive concept are shown. The inventive concept may, however, be embodied in many different forms and should not be construed as limited to the embodiments and aspects set forth herein; rather, the embodiments are provided by way of example so that this disclosure will be thorough and complete, and will fully convey the scope of the inventive concept to those skilled in the art. Accordingly, it is to be understood that the present inventive concept is not limited to the embodiments described herein and illustrated in the drawings; rather, the skilled person will recognize that many changes and modifications may be made within the scope of the appended claims. Like reference numerals refer to like elements throughout the description.

Figure 1:
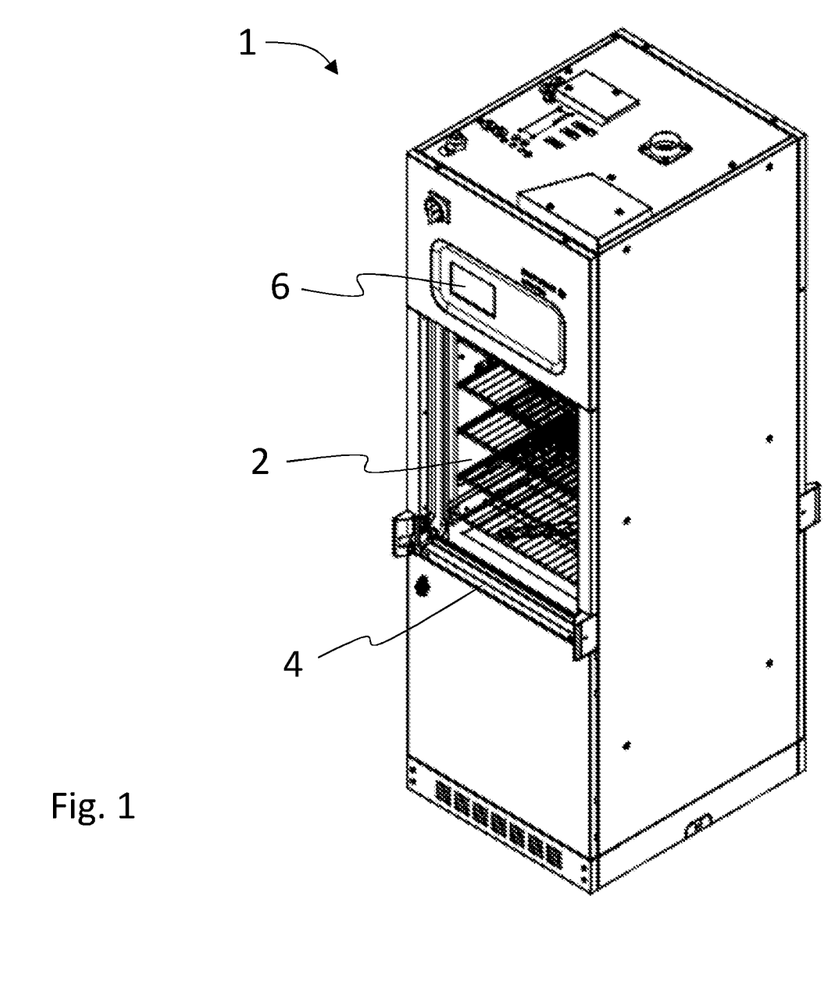
FIG. 1 is a perspective view of one type of medical washer/disinfector in which methods according to the present inventive concept may be implemented.

FIG. 1 is a perspective view of one type of medical washer/disinfector 1 in which methods according to the present inventive concept may be implemented. This example is a smaller single door washer/disinfector. The medical washer/disinfector 1 comprises a washing chamber 2 for receiving medical articles. The washing chamber can be closed by means of a slidable door 4, which is currently in a lowered position to allow access to the washing chamber 2, but which can be raised for closing. A user interface 6, such as a control panel, may be provided for displaying information and enabling a user to select a program.

Figure 2:
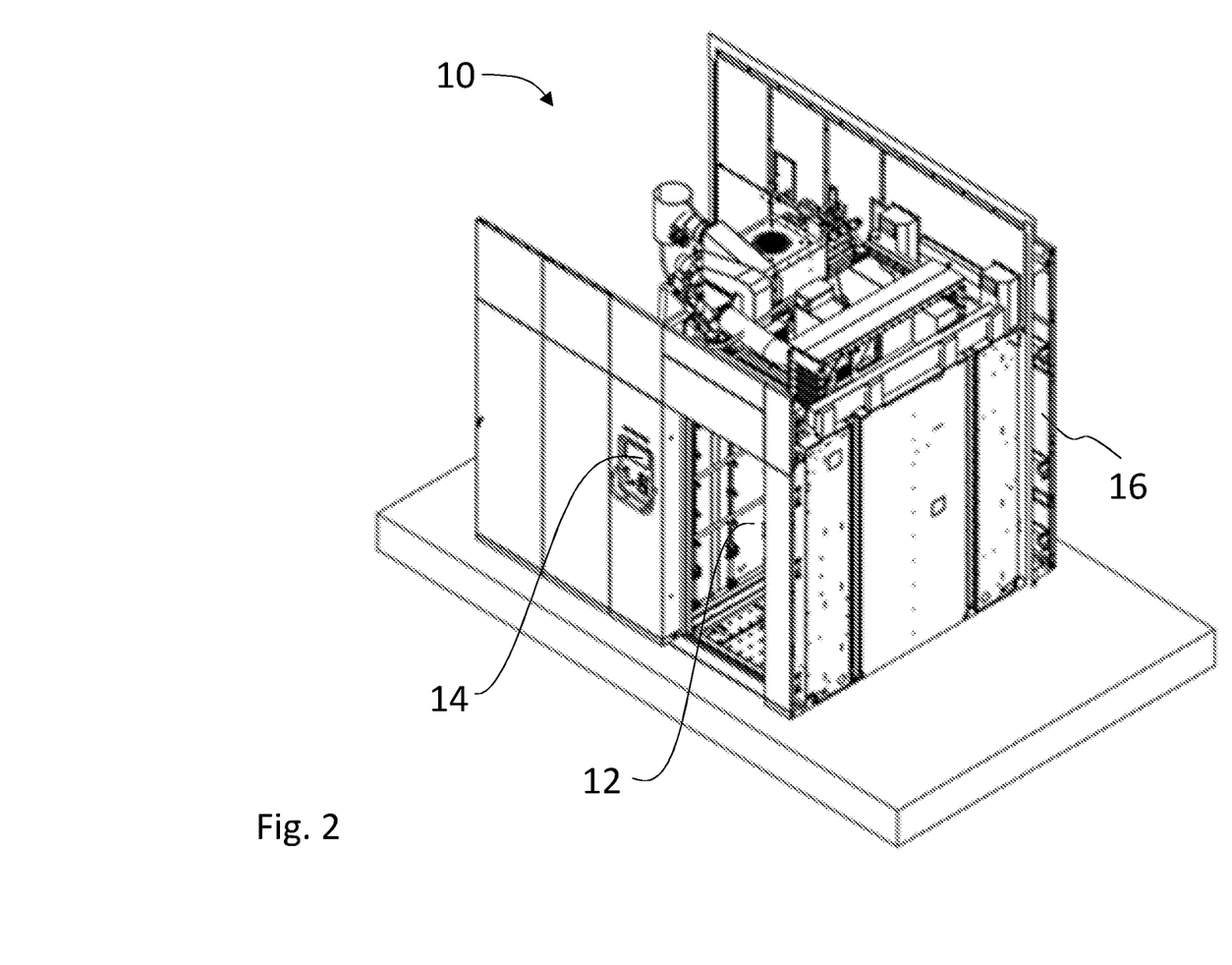
FIG. 2 is a perspective view of parts of another type of medical washer/disinfector in which methods according to the present inventive concept may be implemented.

FIG. 2 is a perspective view of parts of another type of medical washer/disinfector 10 in which methods according to the present inventive concept may be implemented. Compared to the type shown in FIG. 1, the medical washer/disinfector 10 in FIG. 2 is larger. In particular, it has a large washing chamber 12 which is configured to receive wash carts that can be rolled into the washing chamber 12 from one side (a "dirty" side) and, after the washing/disinfecting program is completed, be rolled out at the opposite side (the "clean" side). Thus, the medical washer/disinfector 10 has an entrance and an exit for the wash cart, or for one or more large items to be processed. The space defined by the washing chamber 12 in this example is comparable to a large closet, enabling a person to walk in. A user interface 14, such as a control panel, is provided for program selection and information display. In the present illustration, the user interface 14 is located next to the entrance. Although only one door 16 is visible in the drawing, at the exit, there is also provided another door for closing the entrance to the washing chamber 12. The door at the entrance may suitably be slid sideways between an open and a closed position. In the open position, the door may be located behind the wall portion in which the user interface 14 is provided. This type of two door washer/disinfector may be positioned through a wall which divides different rooms or areas of a medical central sterile services department (CSSD), typically a "dirty" side and a "clean" side. In some embodiments, this type of washer/disinfector will include two circulation pumps, one for supplying circulating liquid ceiling and/or wall sprayers, and another for supplying circulating liquid to a wash cart having one or more cart sprayers. There may be an interface on an inner surface of the washing chamber 12 for temporarily connecting a supply of circulating pumped liquid to wash carts inside the washing chamber.

Figure 3:
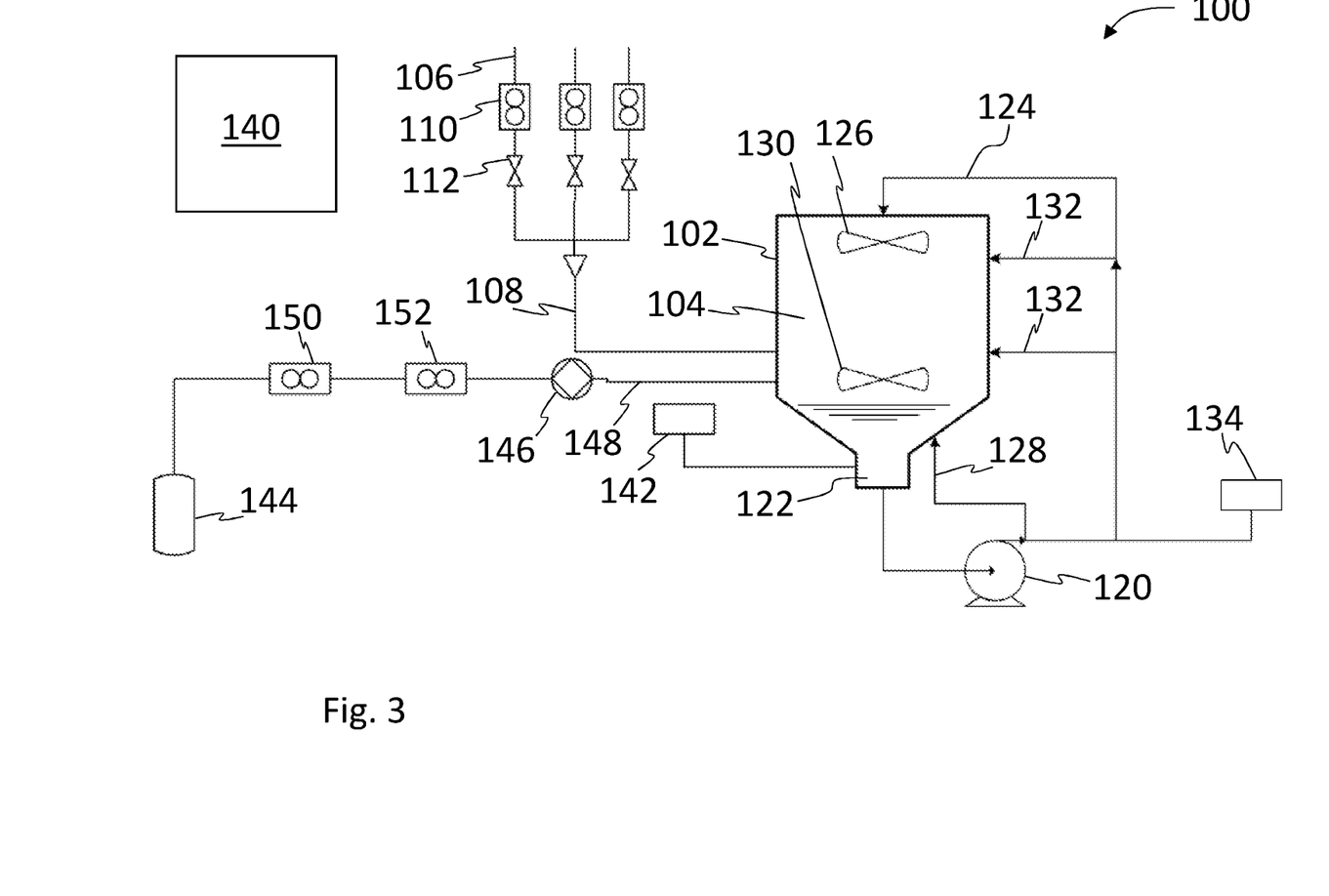
FIG. 3 illustrates schematically a medical washer/disinfector in relation to which a method of filling in accordance with at least one exemplary embodiment will be discussed below.

FIG. 3 illustrates schematically a medical washer/disinfector 100, in relation to which a method of filling may be performed, in accordance with at least one exemplary embodiment. For instance, the schematically illustrated medical washer/disinfector may be one of the types illustrated in FIGS. 1 and 2, or of a different type. The medical washer/disinfector 100 comprises a housing 102 which defines an internal washing chamber 104 for receiving medical articles to be washed/disinfected. Liquid may be fed to the washing chamber 104 from one or more sources 106 via one or more liquid inlet lines 108. In the illustrated example, there are shown three sources of liquid 106, for example cold water, hot water and deionized water. Liquid flowmeters 110 are provided to measure the flow from each source 106 and valves 112 are provided to regulate the flow from the respective sources 106. In the illustrated example, the flows of liquid from the three sources 106 are joined in one common liquid inlet line 108 for feeding liquid into the washing chamber 104. It would, however, be conceivable to have an individual liquid inlet line for each source 106.

A circulation pump 120 is provided for circulating the liquid to and from the washing chamber 104. The circulation pump 120 is configured to draw liquid from the bottom 122 of the washing chamber 104 and to move the liquid through various return conduits 124, 128, 132. In the illustrated example there is one return conduit 124 leading to an upper spray wing 126, the upper spray wing 126 being rotatable and having nozzles for distributing the recirculated liquid. Similarly, there is another return conduit 128 leading to a lower spray wing 130, having corresponding functionality as the upper spray wing 126. Although an upper and a lower spray wing 126, 130 has been illustrated, it should be understood that in other exemplary embodiments, the number of spray wings may be different, as may there locations be. For example, it would be conceivable to have a sprayers at a lateral side wall of the housing 102. The washing chamber 104 may suitably be configured and dimensioned to receive a wash cart, in which case at least one of the remaining return conduits 132 may lead to and be connectable to a manifold of the wash cart. Other conceivable options is to provide return conduits which lead to nozzles in the housing wall or ceiling.

The medical washer/disinfector 100 may be provided with a pressure sensor 134 for measuring the pressure of the fluid leaving the circulation pump 120. The pressure sensor 134 may suitably communicate the sensed pressure to a control unit 140, which may set an alarm or provide an alerting signal in case of inadvertent loss of pressure, and/or interrupt an ongoing processing cycle.

In order to not obscure the legibility of the drawing, the control unit 140 has simply been illustrated as a separate component. It should, however, be understood that the control unit may be appropriately operatively connected, such as by wired or by wireless communication means, to various other components of the medical washer/disinfector 100, including the previously mentioned flowmeters 110, valves 112 and pressure sensor 134.

Furthermore, the control unit 140 also communicates with the circulation pump 120. In particular, the control unit 140 is configured to control the pump speed of the circulation pump 120. It should be understood that the control unit 140 may include one or more distributed processing circuits, electronic memories, etc. and does not necessarily have to be confined to one common location within the medical washer/disinfector 100.

The medical washer/disinfector 100 comprises one or more level sensors 142, which may be digital or analog. Such level sensors 142 are provided for measuring the liquid level within the washing chamber 104. The level sensors 142 may measure the rising level continuously, or detecting the rising level locally at certain heights along the washing chamber 104. The one or more level sensors 142 are configured to communicate the sensed level to the control unit 140.

The medical washer/disinfector 100 may suitably also comprise a source of an additive 144, such as a detergent, and a dosing pump 146 for administering the additive via an additive inlet line 148 into the washing chamber 104. One or more additive flowmeters 150, 152 may suitably be provided for measuring the amount of additive that is supplied into the washing chamber 104. In the illustrated example, one additive flowmeter 150 may be a standard controlling flowmeter, which communicates with the control unit 140 for providing information to the control unit 140 of the amount of additive that is supplied into the washing chamber 104. The other additive flowmeter 152 may be an optional redundant/monitoring flowmeter, wherein in case there is a discrepancy in the measurements of the two additive flowmeters 150, 152 (outside a certain tolerance range), an alarm or alerting signal may be activated, and/or the control unit 140 may disrupt the current processing cycle.

An aspect of the present inventive concept provides a method of filling a medical washer/disinfector, such as the medical washer/disinfector 100 illustrated in FIG. 3. The method comprises determining a desired pump speed for a phase of a process cycle. This may, for instance, be achieved by an operator selecting a certain program which includes one or more process cycles. Each process cycle may include several phases. For any phase that is preceded by filling the medical washer/disinfector 100, the control unit 140 may determine a desired pump speed for that specific phase. The control unit 140 may, for instance, access a lookup table, or make calculations based on various input parameters (e.g. provided by the operator and/or sensed by sensors, such as load sensors, etc.), in order to determine the desired pump speed that the circulation pump 120 should have during said phase.

The method also comprises identifying a predefined filling level in the washing chamber 104 associated with the desired pump speed. This may suitably be done by the control unit 140 and/or one or more level sensors 142, and again, this may be achieved by accessing a lookup table, of by making calculations, or in any other suitable manner. On the one hand, the predefined filling level should be high enough to avoid the risk of cavitation occurring when the circulation pump 120 is running at said desired pump speed during said phase. On the other hand, the predefined level may be kept sufficiently low to avoid excessive overconsumption of liquid (and of additive which is normally based on the amount of liquid used).

The method also comprises feeding liquid into the washing chamber 104 while the circulation pump 120 is running at less than said desired pump speed. In some applications, liquid has already been fed (from one or more of said liquid sources 106 via the liquid inlet line 108) into the washing chamber 104 before the circulation pump 120 is started. The control unit 140 may, for example regulate the different valves 112 for supplying liquid into the washing chamber 104. Furthermore, the liquid level in the washing chamber 104 is suitably at such height that when the circulation pump 120 is started then it will cause no cavitation. This may suitable be checked by means of said one or more level sensors 142. The starting speed of the circulation pump 120 is thus typically a lower speed than said desired pump speed. According to the above, while the circulation pump 120 is running at this lower speed, liquid is fed into the washing chamber 104, thereby causing the liquid level to rise.

The method also comprises, while continuing to feed liquid into the washing chamber 104 so that the liquid level rises, controlling the pump speed to be increased based on the rising liquid level until said desired pump speed is reached. Thus, as the one or more level sensors 142 detect the rising level, either continuously or at checkpoints, the pump speed of the circulation pump 120 may be increased in a controlled manner. It should be noted that rather than relying on information from the liquid flowmeters 110 to control filling, which reveal the amount of liquid that has been supplied into the washing chamber 104, relying on the one or more level sensors 142 is more accurate for the purpose of providing only the amount of liquid which is actually required to support the desired pump speed for each particular load of goods. More specifically, since the recirculated liquid which is distributed (e.g. from the spray wings) will land on the load in the washing chamber 104, and the amount of liquid that does not immediately fall back to the bottom 122 of the washing chamber 104 will vary depending on the characteristics of the load, e.g. type and size of load. Therefore, even though the same amount of liquid has been supplied into the washing chamber 104 at two different occasions, the resulting liquid level may be different depending on the load (and pump speed) at each occasion.

The method also comprises, upon detection that the liquid has been filled to the predefined filling level, interrupting the feeding of the liquid into the washing chamber 104. Thus, after the one or more level sensors 142 indicate that the predefined filling level has been reached, the liquid feeding may stop while the circulation pump continues to run. In some embodiments, there may also be a short time delay after the predefined filling level has been first reached when liquid filling continues. This delay (for continued filling) when used can provide a slight surplus of liquid. i.e. a safety margin, in case a certain amount of recirculated liquid does not rapidly fall back to the bottom 122 of the washing chamber 104, in which case the liquid level might drop below the predefined filling level once the liquid level has stabilized with the circulation pump is running. Nevertheless, if the stabilized liquid level is below the predefined filling level, then the control unit 140 may suitably be configured to control more liquid to be fed into the washing chamber 104 in order to reach the predefined filling level.

In order to facilitate the understanding of the inventive concept, and example will now be discussed. For simplicity, in this example, it is assumed that an operator can select between three different programs: lightly soiled, medium soiled and heavily soiled load. The program for lightly soiled load includes a relatively low desired pump speed, the one for medium soiled load includes a medium desired pump speed, and the one for heavily soiled load includes a relatively high desired pump speed. The low desired pump speed is associated with Level 1, a low predefined filling level. The medium desired pump speed is associated with Level 2, a medium predefined filling level. The high desired pump speed is associated with Level 3, a high predefined filling level. The higher the pump speed, the more liquid is required in the bottom 122 of the washing chamber 104 to avoid cavitation effects, as higher pump sped will "pull" more liquid from the bottom 122 of the washing chamber 104.

It should be understood that the desired pump speed for the circulation pump 120 may be less than the maximum working speed of the circulation pump 120. In this example, it is true at least for the low and medium soiled scenarios (Level 1 and Level 2). The high desired pump speed used for the heavily soiled scenario (Level 3), however, may at least in some exemplary embodiments correspond to the maximum working speed for the circulation pump 120 (but it is conceivable that also that speed is less than the maximum working speed).

In this example, for the program for lightly soiled load, Level 1 will be identified as the predefined filing level. Initially, liquid may be filled to Level 1, and the circulation pump 120 is then started at a speed which is even lower speed than said low desired pump speed. Because the circulation pump 120 starts to circulate the liquid, liquid will be drawn from the bottom 122 of the washing chamber 104 and pumped through the return conduits 124, 128, 132. Thus, the liquid level will drop below Level 1. It should be understood that the total volume of liquid necessary for the phase of the process cycle is larger than the volume of the liquid reaching Level 1 at the bottom 122 of the washing chamber 104. The total volume needed includes volumes of liquid in the return conduits 124, 128, 132, in the circulation pump 120 and the liquid stuck on the load. Thus, once the circulation pump 120 is started liquid needs to be fed into the washing chamber 104 to compensate for the liquid which is now distributed in the other parts of the medical washer/disinfector 100.

Therefore, in accordance with the inventive concept, liquid is now fed into the washing chamber 104 while the circulation pump 120 is running at less than the desired pumps speed, in this case said low desired pump speed. The initial even lower speed avoids cavitation effects. Liquid is continued to be feed into the washing chamber 104 and the pump speed may be increased so as to reach the desired pump speed. Upon detection that Level 1 has been reached, the feeding of liquid may be interrupted and the circulation pump 120 may continue to run at the desired pump speed, i.e. said low desired pump speed which has been determined for the lightly soiled load.

Similarly, in case of a heavily soiled load, in which case Level 3 would be identified as the predefined filling level, the initial procedure may be the same. Suitably, Level 1 and Level 2 may function as checkpoints so that if the pump speed has not yet attained the relatively low speed associated with Level 1 when the one or more liquid sensors 142 have detected that the liquid has reached that level, then the control unit 140 may increase the pump speed to that speed. Likewise, if the pump speed has not yet attained the medium speed associated with Level 2 when the liquid has reached that level, then the pump speed may be controlled to be increased to the medium speed. The pump speed may suitably be increased continuously between the different levels, or it may be increased intermittently. Upon detection that Level 3 has been reached, the feeding of liquid may be interrupted (either immediately or a set time thereafter) and the circulation pump may continue to run at the relatively high desired pump speed.

From the above, it can be understood that the step of feeding liquid into the washing chamber 104, may be preceded by initially supplying liquid to the washing chamber 104 while the circulation pump 120 is inactive, detecting that the liquid has reached a predefined pump-starting level in the washing chamber 104, and activating the circulation pump 120 when the liquid has reached the predefined pump-starting level. In the above examples, both for the lightly soiled scenario and the heavily soiled scenario, Level 1 may suitably be the pump-starting level.

As can be further understood from the above explanation, the increasing of the pump speed based on the rising liquid level may suitably comprise filling the washing chamber 104 to a series of specific levels and increasing the pump speed for each specific level that is reached. In the above example in which Level 3 was the predefined filling level, the pump speed may be increased when the liquid has reached Level 1 after the circulation pump 120 has been started, and then increased to a higher pump speed when the liquid has reached Level 2, and finally an increase to the relatively high desired pump speed when the liquid has reached Level 3. It should, however, be understood that controlling the pump speed to be increased based on the rising liquid level may also comprise continuously increasing the pump speed between any two specific levels of said series of specific levels.

Although the above explanations have been given by way of example with reference to three liquid levels, it should be understood that the inventive concept may be implemented in a corresponding manner with other number of levels, be it a lower or a greater number of levels.

Generalizing, in some embodiments, the washer/disinfector has a plurality of different washing/disinfection programs stored thereon, with at least some washing/disinfection programs having different respective desired pump speeds for the circulation pump 120 than other washing/disinfection programs, and each washing/disinfection program having a predefined filling level which is suitable for use with the corresponding desired pump speed. In some applications, a selection of one of the washing/disinfection programs is received before the filling process, and is used to determine the desired pump speed and/or the predefined filling level. The selection of the washing/disinfection program may be by a human user, or may be an automated selection based, for example, on the identity of the goods to be processed.

If the phase of the process cycle for which the filling method is used requires an additive, such as a detergent, then the method may comprise determining for said phase a desired chemical concentration of an additive in the washing chamber 104. The control unit 140 may suitably do this based on a lookup table. The liquid flowmeters 110 provide information to the control unit 140 about the volume of liquid that is fed into the washing chamber 104. Based on the measured volume, the control unit 140 may thus determine the amount of additive to be provided from the source 144 of additive for obtaining said desired chemical concentration. The control unit 140 may then control the dosing pump 146 and check the additive flowmeters 150, 152 to make sure that the right amount of additive is provided into the washing chamber 104. The correct amount of additive is therefore indirectly optimized by the filling methods described elsewhere which first optimize the amount of liquid (such as water) added to the washing chamber.

Figure 4:
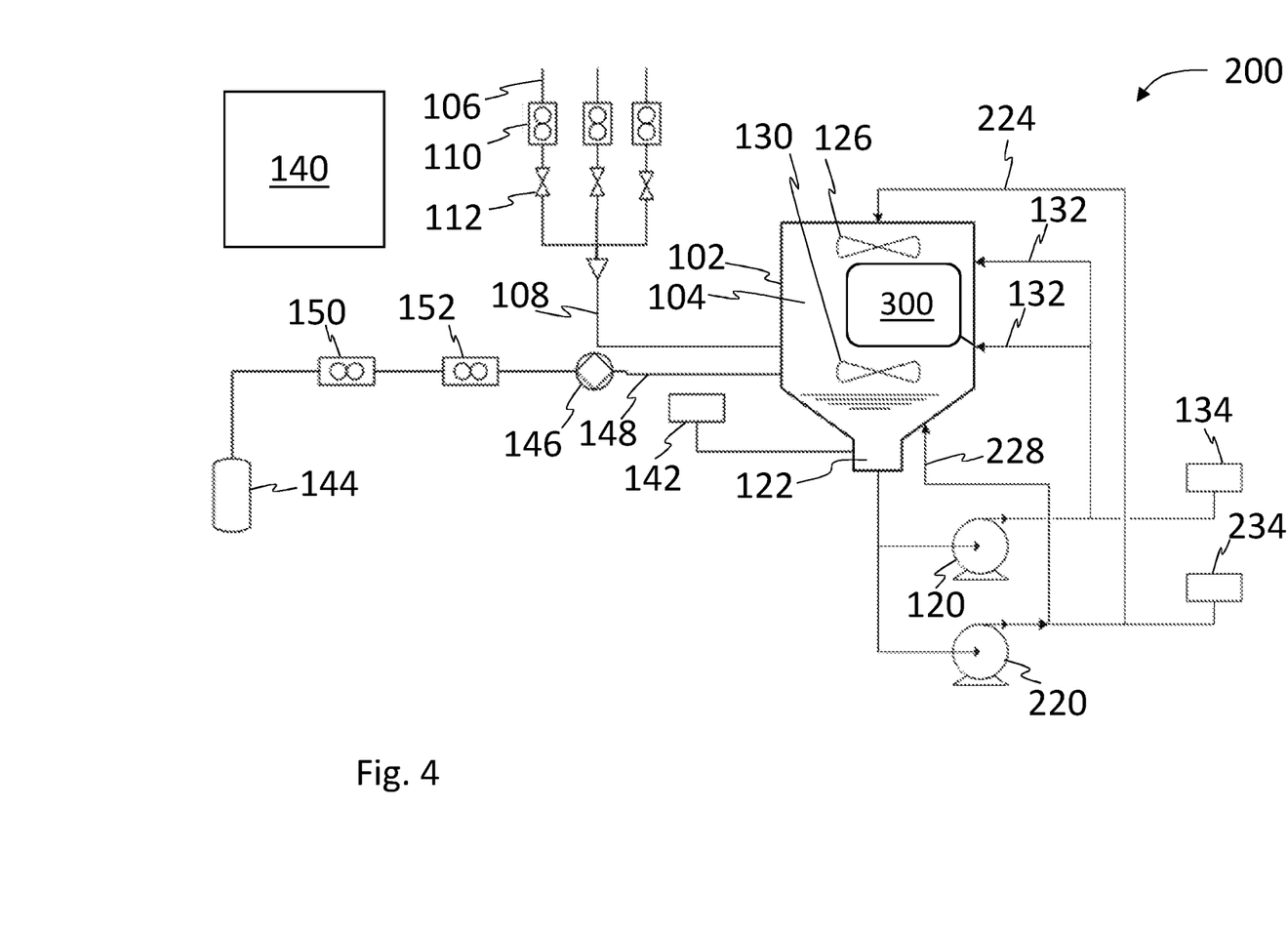
FIG. 4 illustrates schematically another medical washer/disinfector in relation to which a method of filling and a method of operating in accordance with at least some exemplary embodiments will be discussed below.

FIG. 4 illustrates schematically another medical washer/disinfector 200 in relation to which a method of filling and a method of operating in accordance with at least some exemplary embodiments will be discussed below. The medical washer/disinfector 200 may suitably be of the type illustrated in FIG. 2, which in some embodiments receives and supplies fluid to wash carts 300, or another type.

The medical washer/disinfector 200 in FIG. 4 is to a large extent similar to the medical washer/disinfector 100 in FIG. 3, however, an additional circulation pump 220 has been provided. Thus, the medical washer/disinfector 200 in FIG. 4 has a first circulation pump 120, which corresponds to the circulation pump 120 shown in FIG. 3, and a second circulation pump 220. The pump speed of the first circulation pump 120 is controlled in the corresponding manner as discussed in connection with FIG. 3. However, as illustrated in FIG. 4, the fluid pumped by the first circulation pump 120 may suitably be recirculated through only some of the return conduits 132, such as the return conduits 132 that are connectable to a manifold of a wash cart 300 or that are connected to nozzles in the wall or ceiling of the housing 102. The second circulation pump 220 may be arranged to recirculate the fluid through return conduits 224, 228 to the upper and lower spray wings 126, 130. Thus, the first circulation pump 120 may be a wash cart sprayer pump and the second circulation pump 220 may be a chamber sprayer pump. More generally, the first circulation pump and the second circulation pump may each supply liquid to a different respective subset of washer/disinfector sprayers. The first circulation pump 120 and the second circulation pump 220 may be separately controllable by the control unit 140.

The second circulation pump 220 can be kept inactive during the feeding of liquid into the washing chamber 104. Thus, the second circulation pump 220 is not needed during the filling to the predefined filling level. The liquid level obtained during the filling process is based on the liquid level requirements when only the first circulation pump 120 (e.g. wash cart sprayer pump) is running during a subsequent washing/disinfecting process.

A method of operating the medical washer/disinfector 200 of FIG. 4 comprises filling the washing chamber 104 by performing the previously discussed filling method using only the first circulation pump 120, keeping the second circulation pump 220 inactive during the filling. The method or operating the medical washer/disinfector 200 also comprises, after the filling of liquid in the washing chamber 104 has been completed, alternating between activation and inactivation of the second circulation pump 220 in such manner that when the second circulation pump 220 is running, the first circulation pump 120 is controlled to run at a speed that is lower than said desired pump speed or to be inactivated. Thus, by this method of operating, it can be ensured that the total flow of liquid drawn from the bottom 122 of the washing chamber 104 does not surpass the flow achieved with only the first circulation pump 120 running at said desired pump speed. Thus, a desired flow may be maintained, thereby avoiding cavitation effects.

FIG. 4 also illustrates that a pressure switch 234 is provided. The pressure switch 234 is activated in case the output pressure of the liquid from the second circulation pump 220 drops below a set limit value. Suitably, this sets off an alarm and/or the medical washer/disinfector 200 stops its current process cycle. Instead of a pressure switch 234, it would be conceivable to have a pressure sensor similar to the pressure sensor 134 associated with the first circulation pump 120. However, while the first circulation pump 120 may run at different pump speeds, thus different pressures being expected at those different pump speeds, the second circulation pump 220 may suitably just have two states, on/off, wherefore a less expensive pump switch 234 may suffice.

This disclosure includes medical washer/disinfectors, including both one and two door systems, and systems for use with wash carts. This disclosure also includes controllers (comprising electronics and electronic instructions) for controlling washer/disinfectors as described herein. This disclosure further includes methods of operating and controlling washer/disinfectors, methods of efficiently filling washer/disinfectors before washing/disinfection and rinsing cycles, and methods of washing and disinfecting medical goods. It should be understood that various features and methods disclosed herein are contemplated and disclosed in their various combinations and sub-combinations.

The invention claimed is:

1. A method of filling a medical washer/disinfector having a washing chamber for receiving medical articles to be washed/disinfected and a circulation pump for circulating a liquid to and from the washing chamber, the method comprising:
   determining a desired pump speed for a phase of a process cycle,
   identifying a predefined filling level in the washing chamber associated with the desired pump speed,
   feeding liquid into the washing chamber while the circulation pump is running at less than said desired pump speed,
   while continuing to feed liquid into the washing chamber so that a level of the liquid rises, controlling a pump speed to be increased based on the rising level of the liquid until said desired pump speed is reached,
   when the circulation pump is running at said desired pump speed, detecting when the liquid has been filled to the predefined filling level in the washing chamber,
   a predefined time period after detection that the liquid has been filled to the predefined filling level, interrupting the feeding of the liquid into the washing chamber, the predefined time period being in the range of 0.5-10 seconds;
   after interrupting the feeding of the liquid into the washing chamber, allowing the level of the liquid in the washing chamber to stabilize while the circulation pump is running; and
   if the stabilized level of the liquid is below the predefined filling level, feeding more liquid into the washing chamber in order to reach the predefined filling level.

2. The method as claimed in claim 1, wherein the step of feeding liquid into the washing chamber is preceded by the steps of:
   initially supplying liquid to the washing chamber while the circulation pump is inactive,
   detecting that the liquid has reached a predefined pump-starting level in the washing chamber, and activating the circulation pump at less than said desired pump speed when the liquid has reached the predefined pump-starting level.

3. The method as claimed in claim 1, wherein the step of controlling the pump speed to be increased based on the rising level of the liquid comprises:
filling the washing chamber to a series of specific levels and incrementally increasing the pump speed for each specific level that is reached.

4. The method as claimed in claim 3, wherein the step of controlling the pump speed to be increased based on the rising level of the liquid comprises:
continuously increasing the pump speed between any two specific levels of said series of specific levels.

5. The method according to claim 1, further comprising:
determining for said phase of the process cycle a desired chemical concentration of an additive in the washing chamber,
measuring, by means of a flow sensor, the volume of the liquid that is fed into the washing chamber,
based on the measured volume, determining an amount of said additive to be provided into the washing chamber for obtaining said desired chemical concentration, and
providing said determined amount of additive into the washing chamber.

6. The method according to claim 1, wherein said desired pump speed for the circulation pump is less than a maximum working speed for the circulation pump.

7. The method as claimed in claim 6, the method further comprising running a washing/disinfection cycle after the liquid has been filled to the predefined filling level, wherein said desired pump speed is the maximum speed used for the circulation pump during the washing/disinfection cycle.

8. The method according to claim 1,
wherein the medical washer/disinfector has a plurality of different washing/disinfection programs stored thereon, with at least some washing/disinfection programs having different respective desired pump speeds for the circulation pump than other washing/disinfection programs, and each washing/disinfection program having a predefined filling level which is suitable for use with the respective desired pump speed;
the method further comprising:
before feeding liquid into the washing chamber receiving a selection of one of the washing/disinfection programs, and determining the desired pump speed and the predefined filling level based on the selected washing/disinfection program.

9. The method according to claim 1, wherein the circulation pump is a first circulation pump, the medical washer/disinfector also having a second circulation pump for use after the liquid has been filled to the predefined filling level, the method comprising:
keeping the second circulation pump inactive during the feeding of liquid into the washing chamber.

10. The method as claimed in claim 9,
wherein the washer/disinfector is sized and configured to receive a wash cart holding medical articles to be washed/disinfected in the washing chamber, said wash cart including one or more wash cart sprayers;
wherein the washer/disinfector comprises one or more chamber sprayers on a ceiling and/or walls of the washing chamber;
wherein the washer/disinfector is configured to selectively circulate liquid to the one or more chamber sprayers and/or to the one or more wash cart sprayers when present using the first circulation pump and the second circulation pump, the first circulation pump and the second circulation pump being separately controllable,
wherein the first circulation pump is a wash cart sprayer pump and the second circulation pump is a chamber sprayer pump.

11. A method of operating a medical washer/disinfector having a washing chamber for receiving medical articles to be washed/disinfected and a circulation pump for circulating a liquid to and from the washing chamber, comprising:
filling the washing chamber by performing the method of claim 1,
wherein the circulation pump is a first circulation pump, the medical washer/disinfector further having a second circulation pump, wherein the method of operating the medical washer/disinfector further comprises:
keeping the second circulation pump inactive during the feeding of liquid into the washing chamber, and
after the liquid has been filled to the predefined filling level, alternating between activation and inactivation of the second circulation pump in such manner that when the second circulation pump is running, the first circulation pump is controlled to run at a speed that is lower than said desired pump speed or to be inactivated.

12. A medical washer/disinfector, comprising:
a washing chamber for receiving medical articles to be washed/disinfected,
one or more circulation pumps for circulating a liquid to and from the washing chamber, and
a control unit for controlling performance of the steps of the method as claimed in claim 1.

13. The medical washer/disinfector as claimed in claim 12,
wherein the washer/disinfector is sized and configured to receive a wash cart holding medical articles to be washed/disinfected in the washing chamber, said wash cart including one or more wash cart sprayers;
wherein the washer/disinfector comprises one or more chamber sprayers on a ceiling and/or walls of the washing chamber;
wherein the washer/disinfector is configured to selectively circulate liquid to the one or more chamber sprayers and/or to the one or more wash cart sprayers when present using a first circulation pump and a second circulation pump, the first circulation pump and the second circulation pump being separately controllable.

* * * * *